United States Patent [19]

Gante et al.

[11] 4,289,768
[45] Sep. 15, 1981

[54] PHENOTHIAZINE DERIVATIVES AND A PROCESS FOR THEIR PREPARATION

[75] Inventors: Joachim Gante; Hans-Eckart Radunz; Dieter Orth; Hans-Jochen Schliep; Ernst Schorscher, all of Darmstadt, Fed. Rep. of Germany

[73] Assignee: Merck Patent Gesellschaft mit Beschränkter Haftung, Darmstadt, Fed. Rep. of Germany

[21] Appl. No.: 145,652

[22] Filed: May 2, 1980

[30] Foreign Application Priority Data

May 2, 1979 [DE] Fed. Rep. of Germany ....... 2917650

[51] Int. Cl.³ .................. A61K 31/415; C07D 279/30
[52] U.S. Cl. ..................................... 424/247; 544/39
[58] Field of Search .......................... 549/39; 424/247

[56] References Cited

U.S. PATENT DOCUMENTS 2,591,679  4/1952  Cusic ............................ 544/39 OR

OTHER PUBLICATIONS

Schenker–Herbst, Arzeimittel-Forschung (Drug Research), vol. 5, edited by Ernst Jucker, pp. 484 to 497, Birkhauser Verlag Basel und Stuttgart, Printed in Switzerland (1963).

*Primary Examiner*—John D. Randolph
*Attorney, Agent, or Firm*—Millen & White

[57] ABSTRACT

Phenothiazine derivatives of the formula

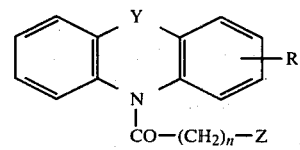

wherein R is H, F, Cl, Br, I, $CH_3$, $CF_3$, CN, $CH_3O$ or $CH_3CO$; Y is S, SO, or $SO_2$; Z is imidazol-1-yl, 2-methyl-imidazol-1-yl, pyrazol-1-yl or benzimidazol-1-yl; and n is 1, 2 or 3; or the physiologically acceptable acid addition salts thereof; are useful as antihypertensive agents, for example.

11 Claims, No Drawings

PHENOTHIAZINE DERIVATIVES AND A PROCESS FOR THEIR PREPARATION

The present invention relates to novel phenothiazine derivatives.

SUMMARY OF THE INVENTION

It is an object of one aspect of this invention to provide novel, pharmaceutically active compounds which can be used for the preparation of medicaments.

Upon further study of the specification and appended claims, further objects and advantages of this invention will become apparent to those skilled in the art.

These objects have been achieved by this invention by providing compounds of Formula I

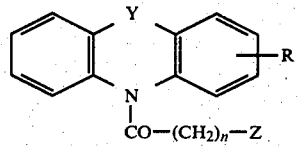

wherein R is H, F, Cl, Br, I, $CH_3$, $CF_3$, CN, $CH_3O$ or $CH_3CO$; Y is S, SO or $SO_2$; Z is imidazol-1-yl, 2-methylimidazol-1-yl, pyrazol-1-yl or benzimidazol-1-yl; and n is 1, 2 or 3, and the physiologically acceptable acid addition salts thereof.

DETAILED DISCUSSION

In Formula I, R is preferably in the 2-position; it can, however, also be in the 1-, 3- or 4-position. Y is preferably S or SO. Z is preferably imidazol-1-yl. n preferably has the value 2.

The preferred R groups are F, Cl and CN, most preferably Cl.

Accordingly, the present invention in one aspect relates especially to those compounds of Formula I in which at least one of the radicals cited has one of the preferred meanings indicated above.

The present invention also relates to a process for preparing the compounds of Formula I and their physiologically acceptable acid addition salts, which comprises (a) reacting a phenothiazine derivative of Formula II

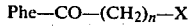
Phe—CO—$(CH_2)_n$—X    (II)

wherein Phe is the radical

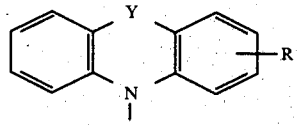

and X is Cl, Br, I, OH or reactive esterified OH and R, Y and n are as defined above, with a base of Formula III

H—Z    (III)

wherein Z is as defined above; or
(b) reacting a phenothiazine derivative of Formula IV Phe—H    (IV)

wherein Phe is as defined above, with a carboxylic acid of Formula V

HOOC—$(CH_2)_n$—Z    (V)

wherein n and Z are as defined above, or with a functional derivative thereof; and (c) optionally oxidizing a resulting phenothiazine of Formula I (Y=S) by treating it with an oxidizing agent to give the corresponding sulphoxide or sulphone of Formula I (Y=SO or $SO_2$);

(d) optionally oxidizing a resulting sulphoxide of Formula I (Y=SO) by treating it with an oxidizing agent to give the corresponding sulphone of Formula I (Y=$SO_2$) and/or (e) converting a resulting base of Formula I by treating it with an acid, into one of its physiologically acceptable acid addition salts.

The compounds of Formula I are prepared in other respects by methods which are in themselves known, e.g., as are described in the literature (for example, in the standard works, such as Houben-Weyl, "Methoden der Organischen Chemie" ("Methods of Organic Chemistry"), Georg-Thieme-Verlag, Stuttgart; Organic Reactions, John Wiley & Sons, Inc., New York), specifically under reaction conditions, e.g., as are known and are suitable for the reactions mentioned. In these methods, it is also possible to make use of variants which are in themselves known but are not mentioned here in greater detail.

The starting materials of Formulae II to V can, if desired, also be formed in situ, by not isolating them from the reaction mixture, but immediately reacting them further to give the compounds of Formula I.

The compounds of Formula I are preferably obtained by reacting phenothiazine derivatives of Formula II with heterocyclic bases of Formula III.

In the phenothiazine derivatives of Formula II, X is preferably Cl or Br; it can, however, also be I, OH or a reactive functionally modified OH group, in particular alkylsulphonyloxy having 1-6 carbon atoms (for example methanesulphonyloxy) or arylsulphonyloxy having 6-10 carbon atoms (for example, benzenesulphonyloxy, p-toluenesulphonyloxy, 1-naphthalenesulphonyloxy or 2-naphthalenesulphonyloxy).

Some of the starting materials of Formulae II and III are known; some are novel. Those of these compounds which are not known can readily be prepared by procedures which are analogous to those used to prepare the known compounds. Thus, the phenothiazine derivatives of Formula II can be obtained by acylating phenothiazines of Formula Phe—H (IV) with carboxylic acids of the formula HOOC—$(CH_2)_n$X or functional derivatives thereof.

The reaction of the compounds of Formulae II and III can be carried out by methods, e.g., which are known from the literature for the N-alkylation of imidazoles, pyrazoles or benzimidazoles. Thus, for example, the components can be melted together in the absence of a solvent, if appropriate in a sealed tube or in an autoclave. It is also possible, however, to react the compounds with one another in the presence of an inert solvent. Examples of suitable solvents include hydrocarbons, such as benzene, toluene or xylene; ketones, such as acetone or butanone; alcohols, such as methanol, ethanol, isopropanol and n-butanol; ethers, such as tetrahydrofuran or dioxane; amides, such as dimethylformamide or N-methylpyrrolidone; nitriles, such as acetonitrile; and, optionally, also mixtures of these solvents with one another or mixtures with water. It can be advantageous to add an acid-binding agent, for example, an alkali metal hydroxide, carbonate or bicarbonate or an alkaline earth metal hydroxide, carbonate or bicarbonate or another salt, with a weak acid, of the alkali metals or alkaline earth metals, preferably of sodium, potassium or calcium, or an organic base, such as triethylamine, dimethylaniline, pyridine or quinoline, or an excess of the base of Formula III. It is also possible to react, for example, chlorine compounds of Formula II (X=Cl) with bases of Formula III in a 1:1 molar ratio to one another in high-boiling solvents, such as toluene or xylene, hydrogen chloride being split off in the form of a gas. Depending on the conditions used, the reaction time is between a few minutes and 7 days, while the reaction temperature is approximately 0°–150° C., normally 60°–130° C.

The compounds of Formula I can also be obtained by acylating a phenothiazine derivative of Formula IV with a carboxylic acid of Formula V or one of its functional derivatives.

The starting materials of Formulae IV and V are also largely known. Insofar as they are not known, they can be prepared by procedures which are analogous to those used to prepare the known compounds. For example, the carboxylic acids of Formula V can be obtained by reacting carboxylic acids of the formula HOOC—$(CH_2)_nX$ with bases of the formula H—Z. Functional derivatives of the carboxylic acids of Formula V are preferably their halides, particularly their chlorides and bromides, and also, for example, their anhydrides and the corresponding acid azides and reactive esters. It is advantageous to carry out the acylation in solution or suspension, and the solvent or suspending agent used can be one or more of those mentioned above. Further examples of suitable solvents include halogenated hydrocarbons, such as 1,2-dichloroethane or chlorobenzene, or esters, such as ethyl acetate. In this acylation, it is also occasionally advantageous to add one of the bases mentioned above, particularly if an acid halide or anhydride of the carboxylic acid of Formula V is used as the acylating agent. If, however, the carboxylic acid itself is used, it is preferable to add a dehydrating agent, for example, a carbodiimide, such as dicyclohexylcarbodiimide. As a rule, the acylation temperatures are −20° to +100°, preferably −5° to +40°. The reaction times can vary from approximately 1 hour to 4 days.

A resulting phenothiazine of Formula I (Y=S) can, if desired, be oxidized to produce the corresponding sulphoxide or sulphone of Formula I (Y=SO or $SO_2$) or a resulting sulphoxide of Formula I (Y=SO) can be oxidized to produce the corresponding sulphone of Formula I (Y=$SO_2$).

Here too, the reaction is carried out by methods which are in themselves known; the details of the reaction conditions can readily be obtained from the literature. If it is desired, for example, to obtain the sulphoxides, oxidation can be carried out, for example, using hydrogen peroxide, per-acids, Cr-VI compounds such as chromic acid, nitric acid, nitrous gases, $N_2O_3$, halogens, such as chlorine, hypochlorites, $KMnO_4$, N-bromosuccinimide, 1-chlorobenztriazole, Ce(IV) compounds, such as $(NH_4)_2Ce(NO_3)_6$, aromatic diazonium salts with negative substituents, such as o-nitrophenyldiazonium chloride or p-nitrophenyldiazonium chloride, or by electrolytic means under relatively mild conditions and at relatively low temperatures (approximately −80° to +100°). If, however, it is desired to obtain the sulphones, the same oxidizing agents are used under more vigorous conditions and/or in excess and, as a rule, at higher temperatures. The customary inert solvents can be present or absent in these reactions. Examples of suitable inert solvents include water, aqueous mineral acids, aqueous alkali metal hydroxide solutions, lower alcohols, such as methanol or ethanol, esters, such as ethyl acetate, ketones, such as acetone, lower carboxylic acids, such as acetic acid, nitriles, such as acetonitrile, hydrocarbons, such as benzene, and chlorinated hydrocarbons, such as chloroform or $CCl_4$.

30% aqueous hydrogen peroxide is a preferred oxidizing agent. Used essentially in the stoichiometric quantity in solvents such as acetic acid, acetone, ethanol or aqueous sodium hydroxide solution, at temperatures of −20° to 100°, it produces the sulphoxides; used in excess at higher temperatures, preferably in acetic acid or in a mixture of acetic acid and acetic anhydride, it produces the sulphones.

Another possible means of preparing the sulphoxides comprises treating the phenothiazines with chlorine, for example, in moist benzene or in acetic acid. The dichloro compounds obtained as intermediates are very readily converted into the sulphoxides by hydrolysis. The sulphoxides are obtained in a similar manner by treating the phenothiazines with sulfuryl chloride, for example, in $CH_2Cl_2$ in the presence of moist silica gel at temperatures of approximately 0° to 30°, preferably at approximately 10°.

It is also possible to oxidize sulphoxides which may have been obtained to produce the sulphones, under more vigorous conditions, and it is not necessary to isolate the sulphoxides.

A resulting base of Formula I can be converted into an appropriate acid addition salt by conventional treatment with an acid. Acids which give physiologically acceptable salts are suitable for this reaction. Thus, it is possible to use inorganic acids, for example, sulphuric acid, hydrogen halide acids, e.g., hydrochloric acid or hydrobromic acid, phosphoric acids, e.g., orthophosphoric acid, nitric acid or sulphamic acid, and also organic acids, specifically, for example, aliphatic, alicyclic, araliphatic, aromatic or heterocyclic monobasic or polybasic carboxylic, sulphonic or sulphuric acids, e.g., formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methanesulphonic or ethanesulphonic acid, ethanedisulphonic acid, 2-hydroxyethanesulphonic acid, benzenesulphonic acid, p-toluenesulphonic acid, naphthalenmonosulphonic and naphthalenedisulphonic acids and laurylsulphuric acid.

If desired, the free bases of Formula I can be liberated from their salts by conventional treatment with a strong base, such as sodium hydroxide or carbonate or potassium hydroxide or carbonate.

It has been found that the compounds of Formula I and their physiologically acceptable acid addition salts have valuable pharmacological properties and are well tolerated. Thus, for example, effects on the circulation, in particular blood pressure lowering activity, are found, and also a diuretic effect.

For example, the substances reduce, to a low level which depends on the dosage, the blood pressure measured at the carotid loop of wake, mongrel dogs (for details of the method compare E. C. van LEERSUM, Pflueger's Archiv 142, 377–395 (1911)) a) in the case of neurogenically hypertensive animals (for details of the method compare K. S. GRIMSON, Archives Surgery 43, 284–305 (1941)), and b) in the case of nephrogenically hypertensive animals (for details of the method compare I. H. PAGE, Science 89, 273–274 (1939)) in a standard test lasting for 10 days with oral administration of doses which can be less than 2.0 mg/kg.

In addition, the blood pressure measured on rats plethysmographically on the tails of wake animals (for method of procedure compare M. GEROLD and H. TSCHIRKY, Arzneimittelforschung 18, 1,285–1,287 (1968)) is also reduced to a lower level during a 4-day oral treatment with the substance administered once a day, specifically, (a) in the case of spontaneously hypertensive rats (strain SHR/NIH-MO/CHB-EMD) and also (b) in the case of rats with DOCA salt-induced hypertension (for method of procedure compare M. GEROLD AND H. TSCHIRKY, loc. cit.).

A test of the blood pressure reaction, carried out as a functional test, after intravenous administration of noradrenalin to normotensive rats which had been given a 4-day oral pretreatment and had then been pithed, for the test, (for details of the method compare R. E. SHIPLEY and J. H. TILDEN, Proc. Soc. Exper. Biol. Med. 64, 453–455 (1947)) showed a reduced reactivity of the vascular system (compare J. KRAETZ et al, Naunyn-Schmiedeberg's Archives of Pharmacol. Supplement to Vol. 302, R 42 (1978)). The determination of the diuretic action of the compounds can be carried out on rats by following the details of W. L. LIPSCHITZ et al, J. Pharmacol, exp. Ther. 79, 97–110 (1943).

The compounds of Formula I and their physiologically acceptable acid addition salts can, therefore, be used as active ingredients in medicaments in human and veterinary medicine for administration, e.g., to mammals including humans, and also as intermediate products for the preparation of other active compounds for medicaments.

Thus, this invention, in another aspect, also relates to the use of the compounds of Formula I and their physiologically acceptable salts in preparation of pharmaceutical formulations, especially by a non-chemical route. In such methods, they can be brought into a suitable dosage form together with at least one excipient or auxiliary and, if appropriate, in combination with one or more additional active compounds.

The invention, in another aspect, also relates to agents, in particular pharmaceutical formulations, containing at least one compound of Formula I and/or one of its physiologically acceptable acid addition salts. These formulations can be employed as medicaments in human or veterinary medicine. Suitable excipients include organic or inorganic substances which are suitable for enteral (for example oral) or parenteral administration or for topical application and which do not react with the novel compounds, for example, water, vegetable oils, benzyl alcohols, polyethylene glycols, gelatin, carbohydrates, such as lactose or starch, magnesium stearate, talc or petroleum jelly. Tablets, dragees, capsules, syrups, elixirs, drops or suppositories are used particularly for enteral administration, solutions, preferably oil-based or aqueous solutions, and also suspensions, emulsions or implants are used particularly for parenteral administration, while ointments, creams or powders are used for topical application. The novel compounds can also be lyophilized and the resulting lyophilizates can be used, for example, for the preparation of injection formulations. The formulations indicated can be sterilized and/or can contain auxiliaries, such as lubricants, preservatives, stabilizers and/or wetting agents, emulsifiers, salts for influencing the osmotic pressure, buffer substances, coloring substances, flavoring substances and/or aroma generating substances. If desired, they can also contain one or more additional active compounds, for example, one or more vitamins.

The present invention, in another aspect, also relates to the use of the compounds of Formula I and their physiologically acceptable acid addition salts in therapeutic treatment of the human or animal body and in combating diseases, in particular all forms of hypertension, and also cardiac, nephrogenic or hepatogenic edemas, ascites, transudation, pregnancy edemas, adiposity with fluid retention and premenstrual and localized edemas, for example, in the case of thrombophlebites, and also for preventing stone formation in the urinary passages. In general, the substances of this invention are administered in analogy to known, commercially available formulations with a similar indication (for example trichlormethiazide or hydrochlorothiazide) preferably in dosages of approximately 1–100 mg, in particular, of 5–50 mg, per dosage unit. The daily dosage is preferably approximately 0.02–5 mg/kg of body weight. The particular dose for each specific patient as usual depends, however, on very diverse factors, for example, on the activity of the particular compound employed, on the age, body weight, general condition of health, sex, diet, etc. of the patient, on the time and route of administration, on the rate of excretion, on the combination of medicaments and on the severity of the particular disease to which the therapy relates. Oral administration is preferred.

Each of the compounds of Formula I mentioned in the Examples which follow is particularly suitable for the preparation of pharmaceutical formulations.

In the Examples which follow, "customary working up" refers to the following procedure:

If necessary, water or dilute sodium hydroxide solution is added; the mixture is extracted with an organic solvent, e.g., chloroform; the phases are separated; the organic extract is evaporated; and the product is purified by chromatography or by crystallization of the base or of one of its salts.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A mixture of 68 g (0.2 mole) of 2-chloro-10-(3-chloropropionyl)-phenothiazine-5-oxide [obtainable by boiling 2-chlorophenothiazine with 3-chloropropionyl chloride in benzene for 12 hours and oxidizing the resulting 2-chloro-10-(3-chloropropionyl)-phenothiazine (melting point 110°–112°) with $H_2O_2$] and 68 g (1 mole) of imidazole is stirred at 110°–115° for 30 minutes. Working up in the customary manner gives 2-chloro-10-[3-(imidazol-1-yl)-propionyl]-phenothiazine-5-oxide, melting point 148°–149°. Hydrochloride, melting point 222°–223°.

EXAMPLE 2

2-Chloro-10-[3-(2-methyl-imidazol-1-yl)-propionyl]-phenothiazine is obtained analogously to Example 1 from 2-chloro-10-(3-p-toluene-sulphonyloxy-propionyl)-phenothiazine and 2-methylimidazole; hydrochloride, melting point 258°–259°.

EXAMPLES 3 TO 45

The following are obtained analogously to Example 1 from the corresponding 10-(chloroacyl)- or 10-(bromoacyl)phenothiazine derivatives and the corresponding bases of Formula III:

3. 10-(Imidazol-1-yl-acetyl)-phenothiazine.
4. 10-(2-Methyl-imidazol-1-yl-acetyl)-phenothiazine.
5. 10-(Pyrazol-1-yl-acetyl)-phenothiazine.
6. 10-(Benzimidazol-1-yl-acetyl)-phenothiazine.
7. 10-[3-(Imidazol-1-yl)-propionyl]-phenothiazine, melting point 150°–152°.
8. 10-[3-(2-Methyl-imidazol-1-yl)-propionyl]-phenothiazine.
9. 10-[3-(Pyrazol-1-yl)-propionyl]-phenothiazine.
10. 10-[3-(Benzimidazol-1-yl)-propionyl]-phenothiazine.
11. 10-[4-(Imidazol-1-yl)-butyryl]-phenothiazine.
12. 10-[4-(2-Methyl-imidazol-1-yl)butyryl]-phenothiazine.
13. 10-[4-(Pyrazol-1-yl)-butyryl]-phenothiazine.
14. 10-[4-(Benzimidazol-1-yl)-butyryl]-phenothiazine.
15. 2-Fluoro-10-[3-(imidazol-1-yl)-propionyl]-phenothiazine, hydrochloride, melting point 244°–246°.
16. 3-Fluoro-10-[3-(imidazol-1-yl)-propionyl]-phenothiazine, hydrochloride, melting point 245°–247°.
17. 1-Chloro-10 -[3-(imidazol-1-yl)-propionyl]-phenothiazine.
18. 2-Chloro-10-(imidazol-1-yl-acetyl)-phenothiazine, melting point 215°–217°.
19. 2-Chloro-10-(2-methyl-imidazol-1-yl-acetyl)-phenothiazine.
20. 2-Chloro-10-(pyrazol-1-acetyl)-phenothiazine.
21. 2-Chloro-10-(benzimidazol-1-yl-acetyl)-phenothiazine.
22. 2-Chloro-10-[3-(imidazol-1-yl)-propionyl]-phenothiazine, melting point 195°–196°. Hydrochloride, melting point 238°–239° (decomposition).
23. 2-Chloro-10-[3-(pyrazol-1-yl)-propionyl]-phenothiazine, hydochloride, melting point 157°.
24. 2-Chloro-10-[3-(benzimidazol-1-yl)-propionyl]-phenothiazine, hydrochloride, melting point 232°–233°.
25. 2-Chloro-10-[4-(imidazol-1-yl)-butyryl]-phenothiazine, melting point 102°–104°.
26. 2-Chloro-10-[4-(2-methyl-imidazol-1-yl)-butyryl]-phenothiazine.
27. 2-Chloro-10-[4-(pyrazol-1-yl)-butyryl]-phenothiazine.
28. 2-Chloro-10-[4-(benzimidazol-1-yl)-butyryl]-phenothiazine.
29. 3-Chloro-10-[3-(imidazol-1-yl)-propionyl]-phenothiazine, hydrochloride, melting point 232°–234° (decomposition).
30. 4-Chloro-10-[3-(imidazol-1-yl)-propionyl]-phenothiazine.
31. 2-Bromo-10-[3-(imidazol-1-yl)-propionyl]-phenothiazine, hydrochloride, melting point 228°–230°.
32. 2-Iodo-10-[3-(imidazol-1-yl)-propionyl]-phenothiazine.
33. 2-Methyl-10-[3-(imidazol-1-yl)-propionyl]-phenothiazine, hydrochloride, melting point 230° (decomposition).
34. 3-Methyl-10-[3-(imidazol-1-yl)-propionyl]-phenothiazine, hydrochloride, melting point 228°–231° (decomposition).
35. 2-Trifluoromethyl-10-(imidazol-1-yl-acetyl)-phenothiazine, hydrochloride, melting point 178°–180°.
36. 2-Trifluoromethyl-10-[3-(imidazol-1-yl)-propionyl]-phenothiazine, melting point 126°–128°.
37. 2-Trifluoromethyl-10-[4-(imidazol-1-yl)-butyryl]-phenothiazine.
38. 2-Cyano-10-[3-(imidazol-1-yl)-propionyl]-phenothiazine, hydrochloride, melting point 260°–263°.
39. 2 Methoxy-10-[3-(imidazol-1-yl)-propionyl]-phenothiazine, hydrochloride, melting point 203°–205°.
40. 3-Methoxy-10-(imidazol-1-yl-acetyl)-phenothiazine.
41. 3-Methoxy-10-[3-(imidazol-1-yl)-propionyl]-phenothiazine, melting point 148°–150°.
42. 3-Methoxy-10-[4-(imidazol-1-yl)-butyryl]-phenothiazine.
43. 2-Acetyl-10-(imidazol-1-yl-acetyl)-phenothiazine.
44. 2-Acetyl-10-[3-(imidazol-1-yl)-propionyl]-phenothiazine, melting point 106°–108°.
45. 2-Acetyl-10-[4-(imidazol-1-yl)-butyryl]-phenothiazine.

EXAMPLE 46

A solution of 14 g of $SO_2Cl_2$ in 65 ml of $CH_2Cl_2$ is added dropwise over the course of 1 hour and at 10° to a mixture of 35.6 g of 2-chloro-10-[3-(imidazol-1-yl)-propionyl]-phenothiazine, 8.2 g of silica gel, 8.2 ml of water and 850 ml of $CH_2Cl_2$. Stirring is continued for 2 hours at 10°; 100 ml of water is added dropwise and the mixture is rendered alkaline by adding $NaHCO_3$. Working up in the customary manner gives 2-chloro-10-[3-(imidazol-1-yl)-propionyl]-phenothiazine-5-oxide, melting point 148°–149°.

EXAMPLES 47 TO 89

The following are obtained analogously to Example 46 by ozidizing the corresponding phenothiazines:

47. 10-(Imidazol-1-yl-acetyl)-phenothiazine-5-oxide.
48. 10-(2-Methyl-imidazol-1-yl-acetyl)-phenothiazine-5-oxide.
49. 10-(Pyrazol-1-yl-acetyl)-phenothiazine-5-oxide.
50. 10-(Benzimidazol-1-yl-acetyl)-phenothiazine-5-oxide.
51. 10-[3-(Imidazol-1-yl)-propionyl]-phenothiazine-5-oxide, melting point 152°–153° C.
52. 10-[3-(2-Methyl-imidazol-1-yl)-propionyl]-phenothiazine-5oxide.
53. 10-[3-(Pyrazol-1-yl)-propionyl]-phenothiazine-5-oxide.
54. 10-[3-(Benzimidazol-1-yl)-propionyl]-phenothiazine-5-oxide.
55. 10-[4-(Imidazol-1-yl)-butyryl]-phenothiazine-5-oxide.
56. 10-[4-(2-Methyl-imidazol-1-yl)-butyryl]-phenothiazine-5-oxide.
57. 10-[4-(Pyrazol-1-yl)-butyryl]-phenothiazine-5-oxide.
58. 10-[4-(Benzimidazol-1-yl)-butyryl]-phenothiazine-5-oxide.
59. 2-Fluoro-10-[3-(imidazol-1-yl)-propionyl]-phenothiazine-5-oxide, fumarate, melting point 95°–97°.

60. 3-Fluoro-10-[3-(imidazol-1-yl)-propionyl]-phenothiazine-5-oxide, hydrochloride, melting point 231°–233°.
61. 1-Chloro-10-[3-(imidazol-1-yl)-propionyl]-phenothiazine-5-oxide.
62. 2-Chloro-10-(imidazol-1-yl-acetyl)-phenothiazine-5-oxide, melting point 162°–163°.
63. 2-Chloro-10-(2-methyl-imidazolyl-acetyl)-phenothiazine-5-oxide.
64. 2-Chloro-10-(pyrazol-1-yl-acetyl)-phenothiazine-5-oxide.
65. 2-Chloro-10-(benzimidazol-1-yl-acetyl)-phenothiazine-5-oxide.
66. 2-Chloro-10-[3-(2-methyl-imidazol-1-yl)-propionyl]-phenothiazine-5-oxide, hydrochloride, melting point 222°–223°.
67. 2-Chloro-10-[3-(pyrazol-1-yl)-propionyl]-phenothiazine-5-oxide, melting point 156°–157°.
68. 2-Chloro-10-[3-(benzimidazol-1-yl)-propionyl]-phenothiazine-5-oxide, melting point 196°–197°.
69. 2-Chloro-10-[4-(imidazol-1-yl)-butyryl]-phenothiazine-5-oxide.
70. 2-Chloro-10-[4-(2-methyl-imidazol-1-yl)-butyryl]-phenothiazine-5-oxide.
71. 2-Chloro-10-[4-(pyrazol-1-yl)-butyryl]-phenothiazine-5-oxide.
72. 2-Chloro-10-[4-(benzimidazol-1-yl)-butyryl]-phenothiazine-5-oxide.
73. 3-Chloro-10-[3-(imidazol-1-yl)-propionyl]-phenothiazine-5-oxide, hydrochloride, melting point 212°–215° (decomposition)
74. 4-Chloro-10-[3-(imidazol-1-yl)-propionyl]-phenothiazine-5-oxide.
75. 2-Bromo-10-[3-(imidazol-1-yl)-propionyl]-phenothiazine-5-oxide.
76. 2-Iodo-10-[3-(imidazol-1-yl)-propionyl]-phenothiazine-5-oxide.
77. 2-Methyl-10-[3-(imidazol-1-yl)-propionyl]-phenothiazine-5-oxide, hydrochloride, melting point 210°–212°.
78. 3-Methyl-10-[3-(imidazol-1-yl)-propionyl]-phenothiazine-5-oxide, hydrochloride, melting point 224°–226° (decomposition).
79. 2-Trifluoromethyl-10-(imidazol-1-yl-acetyl)-phenothiazine-5-oxide.
80. 2-Trifluoromethyl-10-[3-(imidazol-1-yl)-propionyl]-phenothiazine-5-oxide, fumarate, melting point 140° (decomposition).
81. 2-Trifluoromethyl-10-[4-(imidazol-1-yl)-butyryl]-phenothiazine-5-oxide.
82. 2-Cyano-10-[3-(imidazol-1-yl)-propionyl]-phenothiazine-5-oxide, melting point 127°–129°; hydrochloride, melting point 208°–210° (decomposition).
83. 2-Methoxy-10-[3-(imidazol-1-yl)-propionyl]-phenothiazine-5-oxide, fumarate, melting point 90°–94°.
84. 3-Methoxy-10-(imidazol-1-yl-acetyl)-phenothiazine-5-oxide.
85. 3-Methoxy-10-[3-(imidazol-1-yl)-propionyl]-phenothiazine-5-oxide, fumarate, melting point 89°–92°.
86. 3-Methoxy-10-[4-(imidazol-1-yl)-butyryl]-phenothiazine-5-oxide.
87. 2-Acetyl-10-(imidazol-1-yl-acetyl)-phenothiazine-5-oxide.
88. 2-Acetyl-10-[3-(imidazol-1-yl)-propionyl]-phenothiazine-5-oxide, fumarate, melting point 159°–162° (decomposition).
89. 2-Acetyl-10-[4-(imidazol-1-yl)-butyryl]-phenothiazine-5-oxide.

EXAMPLE 90

A mixture of 19.9 g of phenothiazine, 14 g of 3-(imidazol-1-yl)-propionic acid, 20.6 g of dicyclohexylcarbodiimide, and 200 ml of ethyl acetate is stirred for 30 minutes at 0°, and then for 3 hours at 20°. It is worked up in the customary manner to give 10-[3-(imidazol-1-yl)-propionyl]-phenothiazine, melting point 150°–152°.

EXAMPLE 91

A mixture of 25 g of 2-chloro-phenothiazine-5-oxide, 14 g of 3-(imidazol-1-yl)-propionic acid, 20.6 g of dicyclohexylcarbodiimide and 250 ml of tetrahydrofuran is stirred for 1 hour at 0° and then for 2 hours at 30°. It is worked up in the customary manner to give 2-chloro-10-[3-(imidazol-1-yl)-propionyl]-phenothiazine-5-oxide, melting point 148°–149°.

EXAMPLE 92

A mixture of 1 g of 2-chloro-10-[3-(imidazol-1-yl)-propionyl]-phenothiazine, 8 ml of 30% $H_2O_2$ and 40 ml of acetic acid is stirred for 3 hours at 45° and is worked up in the customary manner to give 2-chloro-10-[3-(imidazol-1-yl)-propionyl]-phenothiazine-5,5-dioxide. Melting point 134°–135° decomposition. Hydrochloride, melting point 200°–201°.

EXAMPLES 93 TO 135

The following are obtained analogously to Example 92 by oxidizing the corresponding phenothiazines:
93. 10-(Imidazol-1-yl-acetyl)-phenothiazine-5,5-dioxide.
94. 10-(2-Methyl-imidazol-1-yl-acetyl)-phenothiazine-5,5-dioxide.
95. 10-(Pyrazol-1-yl-acetyl)-phenothiazine-5,5-dioxide.
96. 10-(Benzimidazol-1-yl-acetyl)-phenothiazine-5,5-dioxide.
97. 10-[3-(Imidazol-1-yl)-propionyl]-phenothiazine-5,5-dioxide.
98. 10-[3-(2-Methyl-imidazol-1-yl)-propionyl]-phenothiazine-5,5-dioxide.
99. 10-[3-(Pyrazol-1-yl)-propionyl]-phenothiazine-5,5-dioxide.
100. 10-[3-(Benzimidazol-1-yl)-propionyl]-phnothiazine-5,5-dioxide.
101. 10-[4-(imidazol-1-yl)-butyryl]-phenothiazine-5,5-dioxide.
102. 10-[4-(2-Methyl-imidazol-1-yl)-butyryl]-phenothiazine-5,5-dioxide.
103. 10-[4-(Pyrazol-1-yl)-butyryl]-phenothiazine-5,5-dioxide.
104. 10-[4-(Benzimidazol-1-yl)-butyryl]-phenothiazine-5,5-dioxide.
105. 2-Fluoro-10-[3-(imidazol-1-yl)-propionyl]-phenothiazine-5,5-dioxide.
106. 3-Fluoro-10-[3-(imidazol-1-yl)-propionyl]-phenothiazine-5,5-dioxide.
107. 1-Chloro-10-[3-(imidazol-1-yl)-propionyl]-phenothiazine-5,5-dioxide.
108. 2-Chloro-10-(imidazol-1-yl-acetyl)-phenothiazine-5,5-dioxide.
109. 2-Chloro-10-(2-methyl-imidazolyl-acetyl)-phenothiazine-5,5-dioxide.
110. 2-Chloro-10-(pyrazol-1-yl-acetyl)-phenothiazine-5,5-dioxide.
111. 2-Chloro-10-(benzimidazol-1-yl-acetyl)-phenothiazine-5,5-dioxide.

112. 2-Chloro-10-[3-(2-methyl-imidazol-1-yl)-propionyl]-phenothiazine-5,5-dioxide, hydrochloride, melting point 224° (decomposition).
113. 2-Chloro-10-[3-(pyrazol-1-yl)-propionyl]-phenothiazine-5,5-dioxide.
114. 2-Chloro-10-[3-(benzimidazol-1-yl)-propionyl]-phenothiazine-5,5-dioxide.
115. 2-Chloro-10-[4-(imidazol-1-yl)-butyryl]-phenothiazine-5,5-dioxide.
116. 2-Chloro-10-[4-(2-methyl-imidazol-1-yl)-butyryl]-phenothiazine-5,5-dioxide.
117. 2-Chloro-10-[4-(pyrazol-1-yl)-butyryl]-phenothiazine-5,5-dioxide.
118. 2-Chloro-10-[4-(benzimidazol-1-yl)-butyryl]-phenothiazine-5,5-dioxide.
119. 3-Chloro-10-[3-(imidazol-1-yl)-propionyl]-phenothiazine-5,5-dioxide.
120. 4-Chloro-10-[3-(imidazol-1-yl)-propionyl]-phenothiazine-5,5-dioxide.
121. 2-Bromo-10-[3-(imidazol-1-yl)-propionyl]-phenothiazine-5,5-dioxide.
122. 2-Iodo-10-[3-(imidazol-1-yl)-propionyl]-phenothiazine-5,5-dioxide.
123. 2-Methyl-10-[3-(imidazol-1-yl)-propionyl]-phenothiazine-5,5-dioxide.
124. 3-Methyl-10-[3-(imidazol-1-yl)-propionyl]-phenothiazine-5,5-dioxide.
125. 2-Trifluoromethyl-10-(imidazol-1-yl-acetyl)-phenothiazine-5,5-dioxide.
126. 2-Trifluoromethyl-10-[3-(imidazol-1-yl)-propionyl]-phenothiazine-5,5-dioxide.
127. 2-Trifluoromethyl-10-[4-(imidazol-1-yl)-butyryl]-phenothiazine-5,5-dioxide.
128. 2-Cyano-10-[3-(imidazol-1-yl)-propionyl]-phenothiazine-5,5-dioxide, melting point 139°-142°(decomposition). Hydrochloride, melting point 220° (sintering above 215°).
129. 2-Methoxy-10-[3-(imidazol-1-yl)-propionyl]-phenothiazine-5,5-dioxide.
130. 3-Methoxy-10-(imidazol-1-yl-acetyl)-phenothiazine-5,5-dioxide.
131. 3-Methoxy-10-[3-(imidazol-1-yl)-propionyl]-phenothiazine-5,5-dioxide, hydrochloride, melting point 125° (decomposition).
132. 3-Methoxy-10-[4-(imidazol-1-yl)-butyryl]-phenothiazine-5,5-dioxide.
133. 2-Acetyl-10-(imidazol-1-yl-acetyl)-phenothiazine-5,5-dioxide.
134. 2-Acetyl-10-[3-(imidazol-1-yl)-propionyl]-phenothiazine-5,5-dioxide.
135. 2-Acetyl-10-[4-(imidazol-1-yl)-butyryl]-phenothiazine-5,5-dioxide.

EXAMPLES 136 TO 222

Analogously to Example 1, there are obtained from the corresponding 10-(chloro-acyl)- or 10-(bromo-acyl)-phenothiazine-5-oxides or from the corresponding 10-(chloro-acyl)- or 10-(bromo-acyl)-phenothiazine-5,5-dioxides by reaction with the corresponding bases of Formula III the sulfoxides described in Examples 47 to 89 and the sulfones described in Examples 92 to 135.

EXAMPLES 223 TO 352

Analogously to Example 90 or 91, there are obtained from the corresponding phenothiazines, phenothiazine-5-oxides and phenothiazine-5,5-dioxides of Formula IV with the corresponding carboxylic acids of the Formula V, the compounds described in Examples 2 to 6, 8 to 45, 47 to 89 and 92 to 135.

EXAMPLE 353

A mixture of 1 g of 2-chloro-10-[3-(imidazol-1-yl)-propionyl]-phenothiazine-5-oxide, 4 ml of 30% H₂O₂ and 40 ml of acetic acid is stirred for 3 hours at 45° and is worked up in the customary manner to give 2-chloro-10-[3-(imidazol-1-yl)-propionyl]-phenothiazine-5,5-dioxide, melting point 134°–135° (decomposition). Hydrochloride, melting point 200°–201°.

The following examples relate to pharmaceutical formulations containing compounds of Formula I:

EXAMPLE A: TABLETS

A mixture of 1 kg of 2-chloro-10-[3-(imidazol-1-yl)-propionyl]-phenothiazine-5,5-dioxide, 4 kg of lactose, 1.2 kg of maize starch, 0.2 kg of talc and 0.1 kg of magnesium stearate is pressed in the customary manner to give tablets, in such a way that each tablet contains 10 mg of active compound.

EXAMPLE B: DRAGEES

Tablets are pressed analogously to Example A and are subsequently coated in a customary manner with a coating consisting of sucrose, wheat starch, talc, tragacanth and colorant.

EXAMPLE C: CAPSULES 5 kg of 2-chloro-10-[3-(imidazol-1-yl)-propionyl]-phenothiazine-5,5-dioxide are filled into hard gelatin capsules in a customary manner, so that each capsule contains 20 mg of the active compound.

Tablets, dragees and capsules containing one or more of the remaining active compounds of Formula I and/or their physiologically acceptable acid addition salts, can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A phenothiazine derivative of the formula

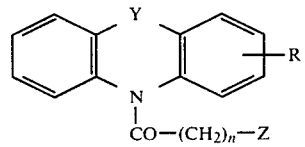

wherein R is H, F, Cl, Br, I, CH₃, CF₃, CN, CH₃O or CH₃CO; Y is S, SO or SO₂; Z is imidazol-1-yl, 2-methylimidazol-1-yl, pyrazol-1-yl or benzimidazol-1-yl; and n is 1, 2 or 3;

or a physiologically acceptable acid addition salt thereof.

2. (a) 2-Chloro-10-[3-(imidazol-1-yl)-propionyl]-phenothiazine;

(b) 2-chloro-10-[3-(imidazol-1-yl)-propionyl]-phenothiazine-5-oxide;

(c) 2-chloro-10-[3-(imidazol-1-yl)-propionyl]-phenothiazine-5,5-dioxide; compounds of claim 1.

3. A compound of claim 1, wherein Z is benzimidazol-1-yl.

4. A compound of claim 1, wherein Y is S or SO.

5. A compound of claim 1, wherein Z is imidazol-1-yl.

6. A compound of claim 1, wherein n is 2.

7. A compound of claim 1, wherein R is in the 2-position.

8. A pharamaceutical composition comprising an antihypertensively effective amount of a compound of claim 1 and a pharmaceutically acceptable carrier.

9. The pharmaceutical composition of claim 8, wherein the amount of the antihypertensive compound is 1–100 mg.

10. A method for treating hypertension in a patient which comprises administering to the patient in need of such treatment an antihypertensively effective amount of a compound of claim 1.

11. A compound of claim 1 wherein Y is $SO_2$.

* * * * *